(12) United States Patent
Kigoshi et al.

(10) Patent No.: US 11,889,989 B2
(45) Date of Patent: Feb. 6, 2024

(54) LIGHT SOURCE APPARATUS FOR ENDOSCOPE, ENDOSCOPE USING THE SAME AND HEAT DISSIPATION METHOD

(71) Applicant: OLYMPUS CORPORATION, Tokyo (JP)

(72) Inventors: Yuri Kigoshi, Sagamihara (JP); Yoshinori Tanaka, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 325 days.

(21) Appl. No.: 17/344,158

(22) Filed: Jun. 10, 2021

(65) Prior Publication Data
US 2021/0298585 A1 Sep. 30, 2021

Related U.S. Application Data

(63) Continuation of application No. PCT/JP2018/046494, filed on Dec. 18, 2018.

(51) Int. Cl.
| | |
|---|---|
| F21V 8/00 | (2006.01) |
| G02B 6/32 | (2006.01) |
| H01S 5/02251 | (2021.01) |
| A61B 1/07 | (2006.01) |
| A61B 1/06 | (2006.01) |
| H01S 5/024 | (2006.01) |

(52) U.S. Cl.
CPC .............. *A61B 1/07* (2013.01); *A61B 1/0676* (2013.01); *G02B 6/0006* (2013.01); *G02B 6/32* (2013.01); *H01S 5/02251* (2021.01); *H01S 5/02476* (2013.01)

(58) Field of Classification Search
CPC ...... A61B 1/07; A61B 1/0676; G02B 6/0006; G02B 6/32; H01S 5/02251; H01S 5/02476
See application file for complete search history.

(56) References Cited

U.S. PATENT DOCUMENTS

| 4,523,806 A | 6/1985 | Kojima et al. |
| 6,099,146 A | 8/2000 | Imamura et al. |

FOREIGN PATENT DOCUMENTS

| JP | S58-123505 A | 7/1983 |
| JP | H02-272414 A | 11/1990 |
| JP | H07-181400 A | 7/1995 |

(Continued)

OTHER PUBLICATIONS

Japanese Office Action dated Jan. 26, 2022 received in 2020-560673.

(Continued)

*Primary Examiner* — Joseph L Williams
(74) *Attorney, Agent, or Firm* — Scully, Scott, Murphy & Presser, P.C.

(57) ABSTRACT

A light source apparatus for endoscope includes a light source, a collective lens, a light shielding member which shields at least a part of the light emitted from the light source, and allows light which is not shielded, to be transmitted as transmitted light, an optical fiber on which, the transmitted light transmitted through the light shielding member is incident, a holding member which includes a heat insulating member, and holds at least one of the light source, the collective lens, and the light shielding member by fixing at a respective position thereof, and a heat exhausting member which exhausts heat generated in the light shielding member to an outside of the holding member.

19 Claims, 14 Drawing Sheets

(56) References Cited

FOREIGN PATENT DOCUMENTS

| JP | H03-51411 U | 8/1998 |
| JP | H10-221605 A | 8/1998 |
| JP | 2001-25889 A | 1/2001 |
| JP | 2005-237542 A | 9/2005 |
| JP | 2007-20855 A | 2/2007 |

OTHER PUBLICATIONS

International Search Report and Written Opinion dated Feb. 26, 2019 received PCT/JP2018/046494.
International Preliminary Report on Patentability dated Jul. 1, 2021 and Written Opinion of the International Searching Authority dated Dec. 18, 2019 received in PCT/JP2018/046494.
Chinese Office Action dated Nov. 30, 2023 received in 201880100065.X.

US 11,889,989 B2

LIGHT SOURCE APPARATUS FOR ENDOSCOPE, ENDOSCOPE USING THE SAME AND HEAT DISSIPATION METHOD

CROSS-REFERENCE TO RELATED APPLICATION

The present application is a continuation application of PCT/JP2018/046494 filed on Dec. 18, 2018; the entire contents of which are incorporated herein by reference.

BACKGROUND

Technical Field

The disclosure relates to a light source apparatus for endoscope, an endoscope using the same and a heat dissipation method.

Description of the Related Art

In an observation by an endoscope, an endoscope distal end portion emits illumination light which illuminates an object. A light source supplies the illumination light. The light supplied by the light source is focused on an end surface of an optical fiber by a lens.

The light incident on the end surface of the optical fiber is guided by the optical fiber up to the endoscope distal end portion. Light emerged from the distal end portion of the endoscope is irradiated to an object as the illumination light.

An arrangement for guiding light emitted from the light source as the illumination light by the optical fiber has been disclosed in Japanese Patent Application Laid-open Publication No. 2005-237542 for example.

In recent years, with an increase in the number of pixels of an image sensor, there has been a tendency of the illumination light becoming even brighter. Consequently, there has also been an increase in the output of the light source. When such light is focused on the end surface of the optical fiber by a lens, the end surface of the optical fiber generates heat at a focusing position.

The arrangement disclosed in Japanese Patent Application Laid-open Publication No. 2005-237542 has a plate for shielding a part of light from the light source in order to reduce the heat generation due to light from a semiconductor laser. This plate has a heat absorbing portion.

SUMMARY

A light source apparatus for endoscope according to at least some embodiments of the present disclosure includes
 a light source configured to emit light,
 a collective lens which focuses the light emitted from the light source,
 a light shielding member which shields at least a part of the light emitted from the light source, and allows light, which is not shielded, to be transmitted as transmitted light,
 an optical fiber on which, the transmitted light transmitted through the light shielding member is incident,
 a holding member which includes a heat insulating member, and holds at least one of the light source, the collective lens, and the light shielding member, by fixing at a respective position thereof, and
 a heat exhausting member which exhausts heat generated in the light shielding member to an outside of the holding member, wherein a thermal resistance value in a thermal path of the light shielding member is smaller than a thermal resistance value of the heat insulating member,
 a thermal resistance value in a thermal path of a connecting portion of the light shielding member and the heat exhausting member is smaller than the thermal resistance value of the heat insulating member, and
 a thermal resistance value in a thermal path of the heat exhausting member is smaller than the thermal resistance value of the heat insulating member.

An endoscope according to at least some embodiments of the present disclosure includes
 the abovementioned light source apparatus for endoscope, and
 an operating section, wherein
 the light source apparatus for endoscope is built-in in the operating section.

Moreover, a heat dissipation method according to at least some embodiments of the present disclosure which is a method of dissipating heat generated in a light shielding member which has shielded a part of light focused toward an incident end of an optical fiber by a collective lens, from light emitted from a light source, includes
 transferring heat to a heat exhausting member by a light shielding member, and
 exhausting heat to an outside of a holding member which holds at least one of the light source, the collective lens, and the light shielding member by fixing at a respective position thereof, by the heat exhausting member.

DETAILED DESCRIPTION

Reasons for and effects of adopting arrangements described below for light source apparatuses for endoscope according to embodiments, and endoscope using the same will be described below by using the accompanying diagrams. For describing specifically advantageous effects of the embodiments, the description will be made by showing specific examples. However, similar to cases of examples to be described below, aspects exemplified are only some of the aspects included in the present disclosure, and these aspects have a large number of variations. Therefore, the present disclosure is not restricted to the aspects exemplified below.

First Embodiment

It is preferable that a light source apparatus for endoscope according to the present embodiment includes a light source which emits light, a collective lens which focuses the light emitted from the light source, a light shielding member which shields at least a part of the light emitted from the light source, and allows light which is not shielded, to be transmitted as a transmitted light, an optical fiber on which the transmitted light transmitted through the light shielding member is incident, a holding member which holds at least one of the light source, the collective lens, and the light shielding member by fixing at a respective position thereof, and a heat exhausting member which exhausts heat generated in the light shielding member to an outside of the holding member.

Figure 1A:
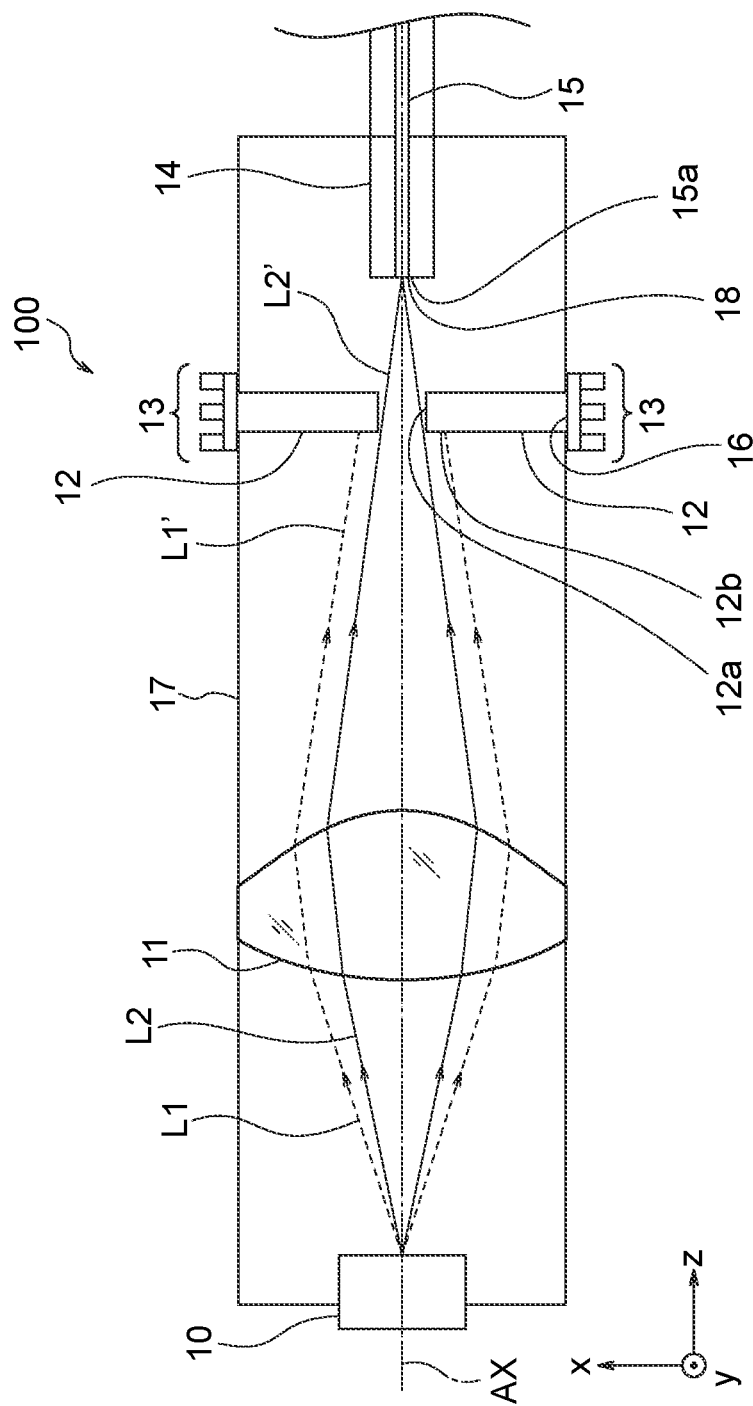
FIG. 1A is a cross-sectional view of a light source apparatus for endoscope of a first embodiment.

FIG. 1A is a cross-sectional view of an arrangement of a light source apparatus for endoscope 100 of the first embodiment. A semiconductor laser 10, which is the light source, emits visible light for example. In the present embodiment, the semiconductor laser 10 emits divergent lights L1 and L2. A collective lens 11 on which, the lights L1 and L2 are incident, has a positive refractive power. Accordingly, the collective lens 11 converts the divergent lights L1 and L2 from the semiconductor laser 10 to convergent lights L1' and L2', and focuses the lights L1' and L2'. A plate 12, which is the light shielding member, shields at least a part L1' after the conversion of the lights L1 and L2 emitted from the semiconductor laser 10. In other words, the plate 12 is a member which reduces a diameter of a light beam from the semiconductor laser 10 to a required diameter. The light L2', which is not shielded by the plate 12, is transmitted through the plate 12 as transmitted light. The light L2' transmitted through the plate 12 is incident on an optical fiber 15. A pigtail 17, which is the holding member, holds at least one of the semiconductor laser 10, the collective lens 11, and the plate 12 by fixing at a respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 12 by fixing at the position thereof. A heat dissipation fin 13, which is the heat exhausting member, exhausts heat generated in the plate 12 to an outside of the plate 12. Details of the heat generation will be described later together with the description of the plate 12.

The convergent light L1' is irradiated to a light shielding portion 12b (an area indicated by oblique lines in FIG. 2A) on the plate 12. When the semiconductor laser 10 having a high output is used, the plate 12 generates heat by shielding the light L1'.

It is desirable to form the plate 12 of a material having a thermal resistance value lower than a thermal resistance value for the pigtail 17, such as, aluminum, brass, and copper. The pigtail 17 is to be formed of a material or a heat insulating material having a high thermal resistance value such as stainless steel for example.

The heat dissipation fin 13 is capable of exhausting heat generated in the plate 12 to an outside of the pigtail 17.

It is preferable that the light source apparatus for endoscope according to the present embodiment has an optical fiber holding member which holds the optical fiber by fixing a position of an incident end of the optical fiber, on the basis of a focusing position of the transmitted light.

A ferrule 14, which is the optical fiber holding member, holds an end surface 15$d$ which is an incident end of the optical fiber 15 by fixing at a position thereof, on the basis of a focusing position 18 of the light L2' transmitted through the plate 12.

By inserting the ferrule 14 into the pigtail 17, it is possible to make the focusing position 18 of the light L2' and a core 15$a$ of the optical fiber 15 coincide.

Figure 1B:
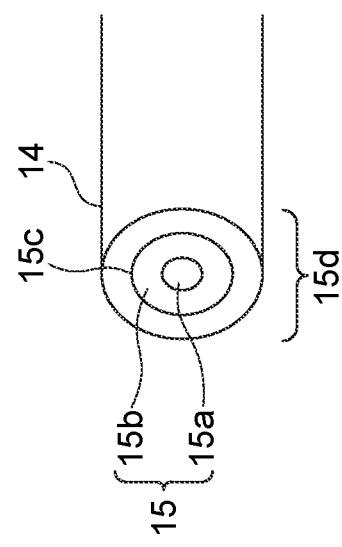
FIG. 1B is a perspective view of an optical fiber end surface.

FIG. 1B is a perspective view of the end surface 15$d$ of the optical fiber 15. The optical fiber 15 has the core 15$a$ which guides light, and a clad 15$b$ which is disposed around an outer peripheral portion of the core 15$a$ and has a refractive index lower than a refractive index of the core 15$a$. The ferrule 14, which is the optical fiber holding member, holds the optical fiber 15 by at least a part of the clad of the optical fiber 15 being glued by an adhesive 15$c$. The plate 12, out of the light from the semiconductor laser 10, allows the light L2' incident on a desired position at a desired angle on the end surface 15$d$ of the optical fiber 15, to be transmitted as transmitted light, and shields and absorbs the light other than the transmitted light. Transmitted light L2' which is transmitted through the plate 12 is incident on the core 15$a$ and the clad 15$b$.

The adhesive 15$c$ is an adhesive which is used for fixing the optical fiber 15 to the ferrule 14. The adhesive 15, for instance, is a thermosetting epoxy adhesive. Moreover, a material of the optical fiber 15 may be any material made of glass or resin.

Consequently, the light L2' is incident only on the end surface 15$d$ of the optical fiber 15, and particularly on the core 15$a$. The light not being irradiated to the adhesive 15$c$ around the optical fiber 15, there is no melting of the adhesive 15$c$ due to heat. Accordingly, it is possible to reduce dirt on the end surface of the optical fiber 15 including the core 15$a$. As a result, it is possible to make the light from the semiconductor laser 10 incident efficiently on the optical fiber 15.

The pigtail 17 includes a heat insulating member. The heat dissipation fin 13 is thermally connected to the plate 12. The term 'thermally connected' refers to a state in which the heat dissipation fin 13 is connected to be in contact with the plate 12 so that the heat is transferred to the plate 12, and a state in which a transfer of heat between the plate 12 and the heat dissipation fin 13 is possible. Moreover, the plate 12 and the heat dissipation fin 13 are held by the pigtail 17. Accordingly, it is possible to transfer efficiently the heat from the plate 12 to the heat dissipation fin 13.

The pigtail 17 is formed by a member (insulating member) having a high thermal resistance value. Accordingly, the heat generated in the plate 12 is not transmitted to the pigtail 17. Furthermore, it is possible to transfer the heat generated in the plate 12 to the heat dissipation fin 13.

A thermal resistance value in a thermal path of the plate 12 is smaller than a thermal resistance value of the insulating member which forms the pigtail 17. A thermal resistance value in a thermal path of the connecting portion 16 of the plate 12 and the heat dissipation fin 13 is smaller than the thermal resistance value of the heat insulating member which forms the pigtail 17.

A thermal resistance value in a thermal path of the heat dissipation fin 13 is smaller than the thermal resistance value of the heat insulating member which forms the pigtail 17.

Accordingly, it is possible to reduce the heat in the plate 12, the connecting portion 16, and the heat dissipation fin 13 from being transmitted to the pigtail 17.

Figure 2A:
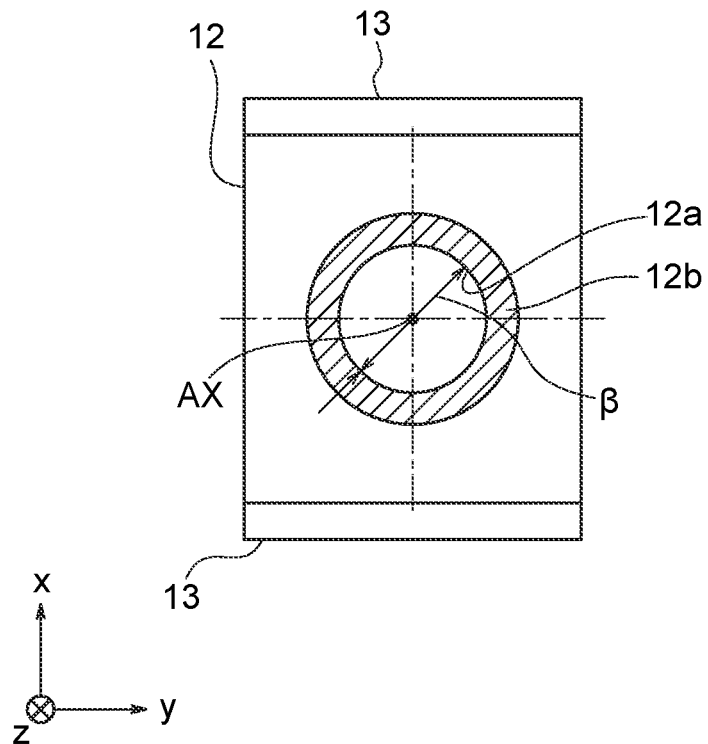
FIG. 2A is a front view of a plate.

A shape of the plate 12 will be described below. FIG. 2A is a front view of the plate 12. The plate 12 has an opening 12a in a part thereof. The plate 12 allows only light passed through the opening 12a to be transmitted through the plate 12 and be incident on the optical fiber 15.

The plate 12 is formed by a light absorbing member, which absorbs light from the semiconductor laser 10, which is irradiated to the light shielding portion 12b other than the opening 12a. The plate 12 is configured to absorb light by performing a black oxide treatment on a surface of the member. For example, in a case in which the material of the plate 12 is aluminum, the light absorbing member is black alumite.

Moreover, a surface of the light absorbing member in the plate 12 has an absorbing characteristic with respect to a visible light band of the light from the semiconductor laser 10. Accordingly, in the plate 12, it is possible to suppress the scattering of the light L1' which is shielded, and to shield the light efficiently.

Accordingly, it is possible to make only the light L2' necessary for illuminating an object, incident on the optical fiber 15.

The plate 12 is disposed between the semiconductor laser 10 and the optical fiber 15.

Particularly, in the present embodiment, the plate 12 is disposed between the collective lens 11 and the optical fiber 15.

The light shielding portion 12b has a shape which shields excess light L1' that is not transmitted through the opening 12a.

The opening 12a has a circular shape having a center which coincides with an optical axis AX of the light from the semiconductor laser 10.

Figure 3:
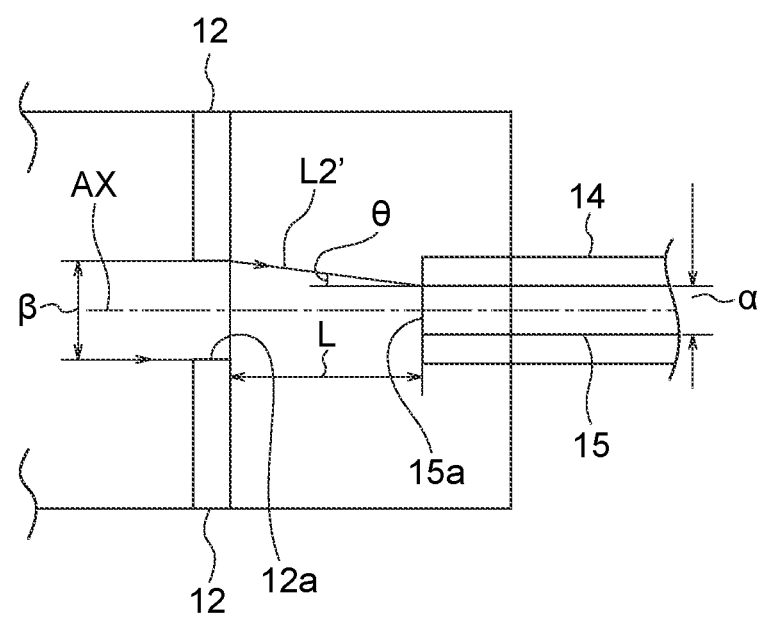
FIG. 3 is a cross-sectional view of a portion from the plate up to a ferrule of the first embodiment.

FIG. 3 is a cross-sectional view of a portion from the plate 12 up to the ferrule 14 of the first embodiment. In the present embodiment, preferably, it is desirable that the light L2' transmitted through the opening 12a is light which is incident on the core 15a (FIG. 1B) of the optical fiber 15. Accordingly, it is possible to make an arrangement such that the adhesive 15c is not melted by the light that has passed through the clad 15b after being incident on the optical fiber 15. Therefore, it is possible to reduce contamination of the end surface 15d of the optical fiber 15 including the core 15a by the adhesive 15c. As a result, it is possible to make the light from the semiconductor laser 10, incident efficiently on the optical fiber 15.

More preferably, the light L2' transmitted through the plate 12 is incident on the optical fiber 15 at an angle not larger than an acceptance angle of the optical fiber 15. In other words, it is desirable that the light L2' is at an angle which is determined by an NA (numerical aperture) of the optical fiber 15. Accordingly, it is possible to use the light from the semiconductor laser 10 effectively.

In the present embodiment, it is preferable that following conditional expression (1) is satisfied.

$$\beta \leq \alpha + 2 \times L \times \tan\theta \quad (1)$$

where,

β denotes a diameter of an opening of a plate,

α denotes a diameter of a core of an optical fiber,

θ denotes the maximum angle of incidence determined by an NA of the optical fiber, and L denotes a distance along an optical axis from an optical fiber end surface up to the plate.

By satisfying conditional expression (1), it is possible to guide effectively the light from the semiconductor laser 10 to the core 15a. Consequently, it is possible to prevent the adhesive 15c from melting due to heat.

Figure 2B:
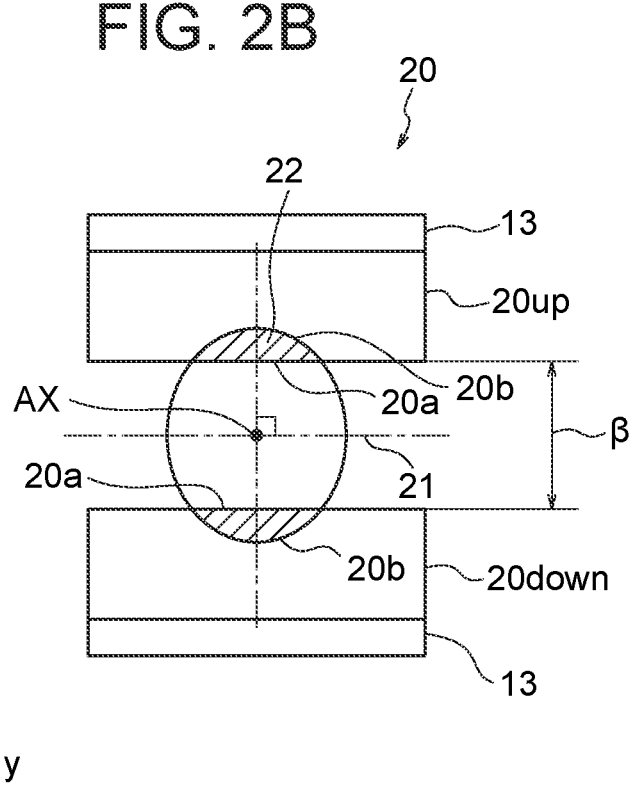
FIG. 2B is a front view of another plate.

Another arrangement example of a plate will be described below. FIG. 2B is a front view of another plate 20.

The plate 20 has openings 20a and 20b formed by two or more than two light shielding plates 20up and 20down disposed to be movable from an outer portion of the pigtail 17. The openings 20a and 20b, out of the light from the semiconductor laser 10, allow more amount of light in a short-axis direction 21 than in a long-axis direction 22 of a light beam cross-section to be transmitted.

The opening 20a has a line symmetric shape with a straight line having a point of intersection with the optical axis AX as an axis of symmetry, in a plane perpendicular to an optical axis AX of the light from the semiconductor laser 10.

In a case in which a cross-sectional shape (intensity distribution) of a light beam from the semiconductor laser 10 is an elliptical shape, the plates 20 up and 20down are to be disposed only in a long-axis direction thereof. In such manner, by making an arrangement such that the two plates can be inserted in a vertical direction (x-direction) in such manner, it is possible to allow the light beam in the short-axis direction 21 of the light beam of which, a cross-section has the elliptical shape, to be transmitted selectively. Accordingly, it is possible to guide effectively the light from the semiconductor laser 10 to the optical fiber 15.

Second Embodiment

Characteristics of a light shielding member, a holding member, and a heat exhausting member in each embodiment described below are same as the characteristics described in the first embodiment, unless specifically mentioned.

Figure 4:
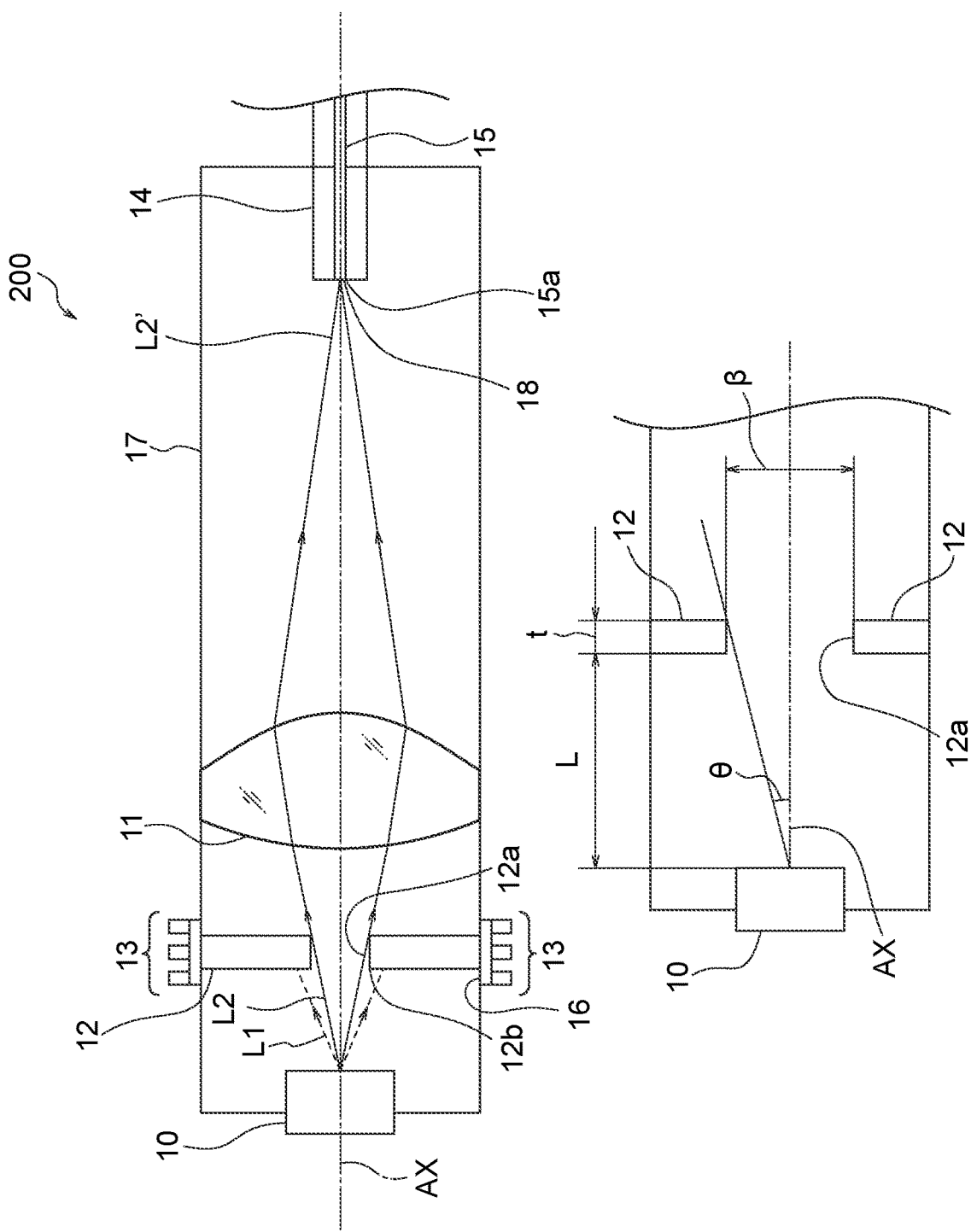
FIG. 4A is a cross-sectional view of a light source apparatus for endoscope of a second embodiment.
FIG. 4B is a cross-sectional view of a portion from a light source up to a plate.

FIG. 4A is a cross-sectional view of an arrangement of a light source apparatus for endoscope 200 of a second embodiment. The semiconductor laser 10, which is the light source, emits visible light, for instance. In the present embodiment, the semiconductor laser 10 emits divergent lights L1 and L2. The plate 12, which is the light shielding member, shields at least a part L1 of the lights L1 and L2 emitted from the semiconductor laser 10. The plate 12 allows light L2, which is not shielded, to be transmitted as transmitted light. The collective lens 11 has a positive refractive power. The collective lens 11 converts the divergent light L2 from the semiconductor laser 10 to convergent light L2' and focuses the convergent light L2'. The light L2' focused by the collective lens 11 is incident on the optical fiber 15. The pigtail 17, which is the holding member, holds at least one of the semiconductor laser 10, the plate 12, and the collective lens 11 by fixing at a respective position thereof. Specifically, the pigtail 17 holds the semiconductor laser 10 by fixing at the position thereof. Moreover, the pigtail 17 holds the plate 12 by fixing at the position thereof. Furthermore, the pigtail 17 holds the collective lens 11 by fixing at the position thereof. The heat dissipation fin 13, which is the heat exhausting member, exhausts heat generated in the plate 12 to an outside of the pigtail 17.

The heat dissipation fin 13 exhausts the heat generated in the light shielding portion of the plate 12 to the outside of the pigtail 17. An example of the light shielding portion 12b is indicated by oblique lines in FIG. 2A. Moreover, an example of the light shielding portion 20b is indicated by oblique lines in FIG. 2b.

The ferrule 14 holds the end surface 15d which is the incident end of the optical fiber 15 by fixing the position thereof, on the basis of the focusing position 18 of the light L2' transmitted through the plate 12.

By inserting the ferrule 14 into the pigtail 17, it is possible to make the focusing position of the light L2' and the core 15a of the optical fiber 15 coincide.

In the present embodiment, the point that the plate 12 is disposed between the semiconductor laser 10 and the collective lens 11 differs from the first embodiment.

FIG. 4B is a cross-sectional view of a portion from the semiconductor laser 10 up to the plate 12. The semiconductor laser 10 emits divergent light.

In the present embodiment, it is desirable to satisfy following conditional expression (2).

$$\beta \leq \alpha + 2 \times (L+t) \times \tan\theta \quad (2)$$

where,

β denotes a diameter of an opening of a plate,

α denotes a diameter of a core of an optical fiber,

θ denotes the maximum angle of incidence determined by an NA of the optical fiber, t denotes a thickness of an optical axis of the plate, and L denotes a distance along an optical axis from an optical fiber end surface up to the plate.

By satisfying conditional expression (2), out of the light from the semiconductor laser 10, it is possible to guide effectively the light L2' not shielded by the plate 12. Furthermore, it is possible to prevent the adhesive 15c (FIG. 1B) from melting due to the heat of the plate 12.

Third Embodiment

Figure 5:
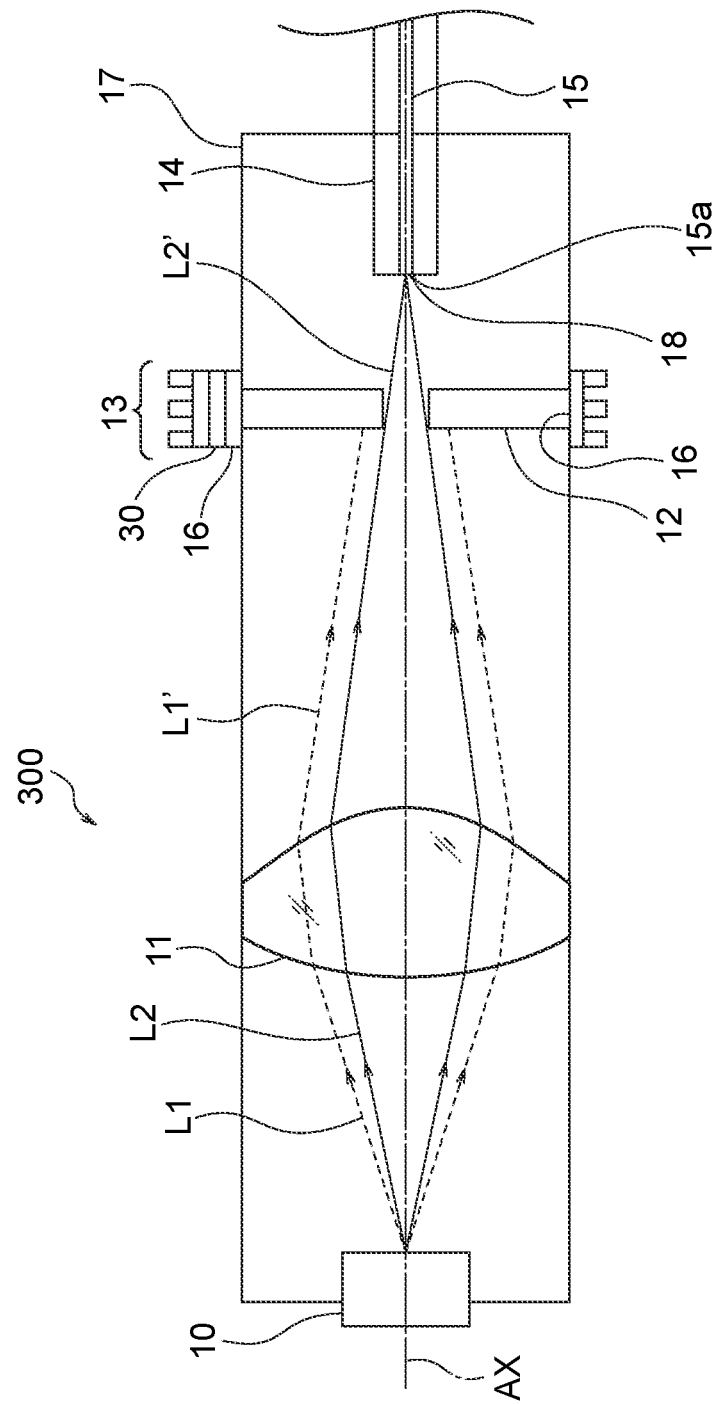
FIG. 5 is a cross-sectional view of a light source apparatus for endoscope of a third embodiment.

FIG. 5 is a cross-sectional view of an arrangement of a light source apparatus for endoscope 300 of a third embodiment. The semiconductor laser 10, which is the light source, emits visible light, for instance. In the present embodiment, the semiconductor laser 10 emits divergent lights L1 and L2. The collective lens 11 has a positive refractive power. The collective lens 11 converts the divergent lights L1 and L2 from the semiconductor laser 10 to convergent lights L1' and L2', and focuses the convergent light L1' and L2'. The plate 12, which is the light shielding member, shields at least a part L1' after conversion of the lights L1 and L2. The light L2' not shielded by the plate 12 is transmitted as transmitted light. The light L2' transmitted through the plate 12 is incident on the optical fiber 15. The pigtail 17, which is the holding member, holds at least one of the semiconductor laser 10, the collective lens 11, and the plate 12 by fixing at a respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 12 by fixing at the position thereof.

A heat exhausting member in the present embodiment is at least one of a heat exchanging member and a heat diverging member. The heat exchanging member actively transfers the heat from the plate 12. The heat diverging member dissipates the heat received, to the surrounding atmosphere. Peltier element is an example of the heat exchanging member. Heat sink and heat dissipation fin are examples of the heat diverging member. In the present embodiment, a Peltier element 30 and the heat dissipation fin 13 are used by connecting.

In the present embodiment, the Peltier element 30 and the heat dissipation fin 13 are fixed via the connecting portion 16 of the plate 12. A current is passed to the Peltier element 30, and a heat-absorbing side is connected to the connecting portion 16 of the plate 12, and a heat generating side is connected to the heat dissipation fin 13. The heat dissipation fin 13 dissipates the heat from the Peltier element 30 to the surrounding atmosphere.

In the present embodiment, out of the light from the semiconductor laser 10, it is possible to guide effectively the light L2' which is not shielded by the plate 12, to the core 15a (FIG. 1B). Furthermore, it is possible to prevent the adhesive 15c (FIG. 1B) from melting due to the heat of the plate 12.

Fourth Embodiment

Figure 6:
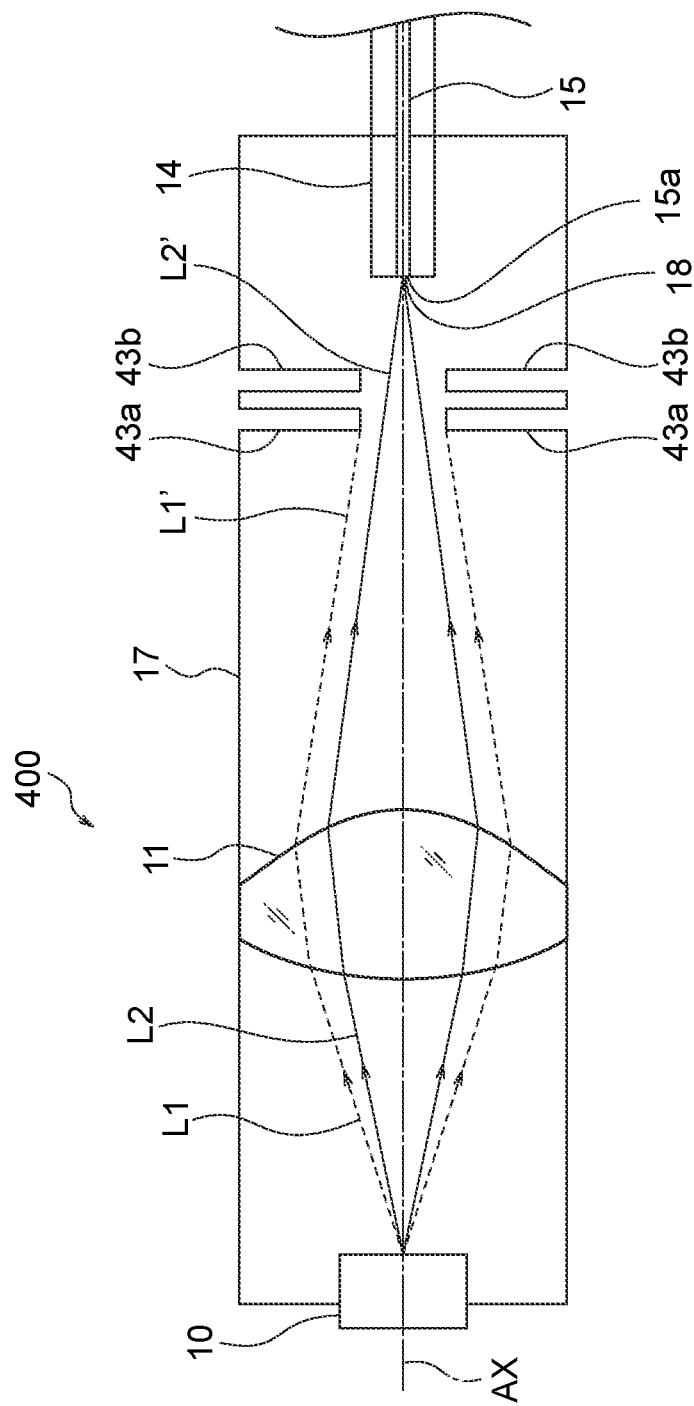
FIG. 6 is a cross-sectional view of a light source apparatus for endoscope of a fourth embodiment.

FIG. 6 is a cross-sectional view of an arrangement of a light source apparatus for endoscope 400 of a fourth embodiment. The heat exhausting member is configured to serve a function of plates 43a and 43b.

The semiconductor laser 10, which is the light source, emits visible light for instance. In the present embodiment, the semiconductor laser 10 emits divergent lights L1 and L2. The collective lens 11 has a positive refractive power. The collective lens 11 converts the divergent lights L1 and L2 from the semiconductor laser 10 to convergent lights L1' and L2', and focuses the lights L1' and L2'. The plates 43a and 43b, which are the light shielding members, shield at least a part L1' after the conversion of the lights L1 and L2 emitted from the semiconductor laser 10. Light L2' which is not shielded by the plates 43a and 43b is transmitted as transmitted light. The light L2' which is transmitted through the plates 43a and 43b is incident on the optical fiber 15. The pigtail 17, which is the holding member, holds at least one of the semiconductor laser 10, the collective lens 11, and the plates 43a and 43b by fixing at a respective position thereof. Specifically, the pigtail 17 holds the semiconductor laser 10 by fixing at the position thereof. Moreover, the pigtail 17 holds the collective lens 11 by fixing at the position thereof.

In the present embodiment, the plates 43a and 43b are a part of the pigtail 17. Accordingly, it is possible to reduce the number of components by integrating the plates 43a and 43b with the pigtail 17.

There is a space in each of the plates 43a and 43b. Accordingly, an area of heat dissipation by the plates 43a and 43b becomes wide. Consequently, it is possible to dissipate efficiently the heat of the plates 43a and 43b to the outside of the pigtail 17.

Moreover, in the present embodiment, the heat exhausting member also serves the function of the plates 43a and 43b. Accordingly, it is possible to reduce the number of components.

Modified Embodiment 1 of Fourth Embodiment

Figure 7:
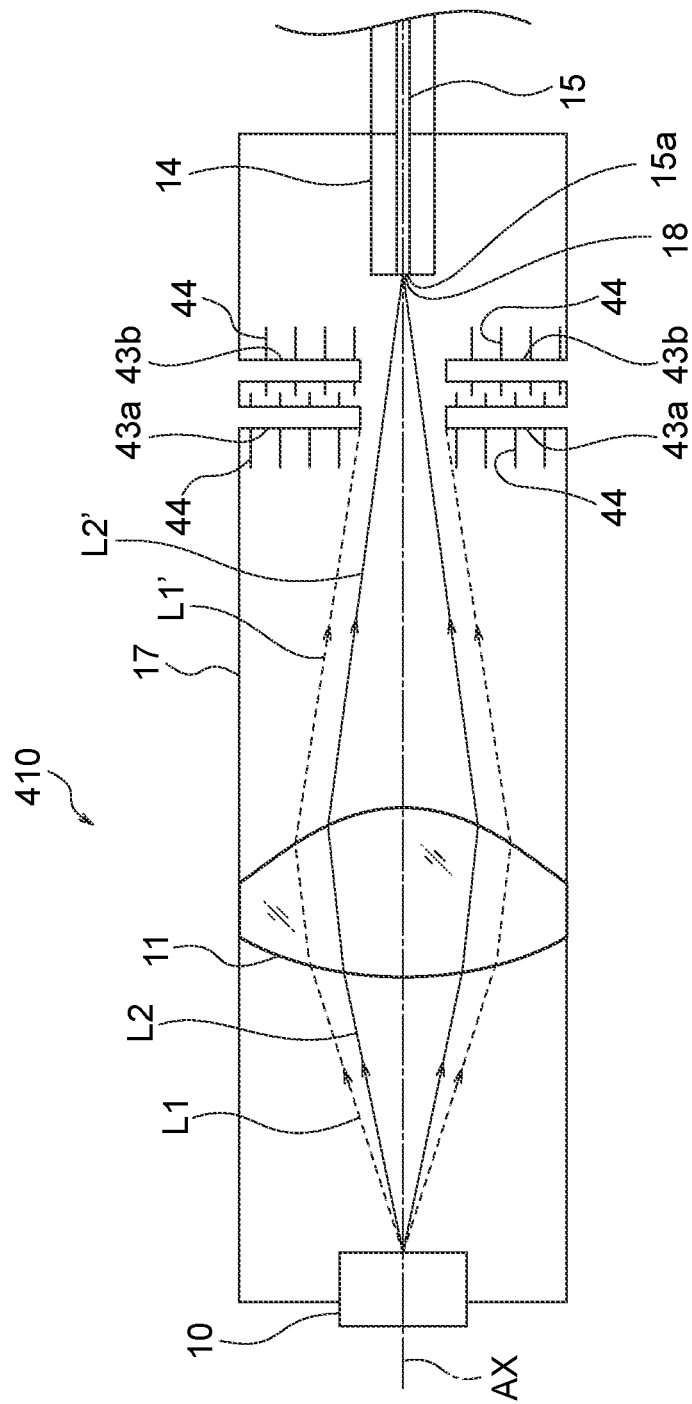
FIG. 7 is a cross-sectional view of a light source apparatus for endoscope of a modified embodiment of the fourth embodiment.

FIG. 7 is a cross-sectional view of an arrangement of a light source apparatus for endoscope 410 of a modified embodiment 1 of the fourth embodiment. In the present modified embodiment, the light exhausting member also serves the function of the plates 43a and 43b. Furthermore, each of the plates 43a and 43b further has a plurality of heat dissipation fins 44. The heat dissipation fins 44 are formed of a material having a high thermal conductivity. Accordingly, the area of heat dissipation by the plates 43a and 43b becomes even wider. Therefore, it is possible to dissipate efficiently the heat of the plates 43a and 43b to the outside of the pigtail 17.

Modified Embodiment 2 of Fourth Embodiment

Figure 8:
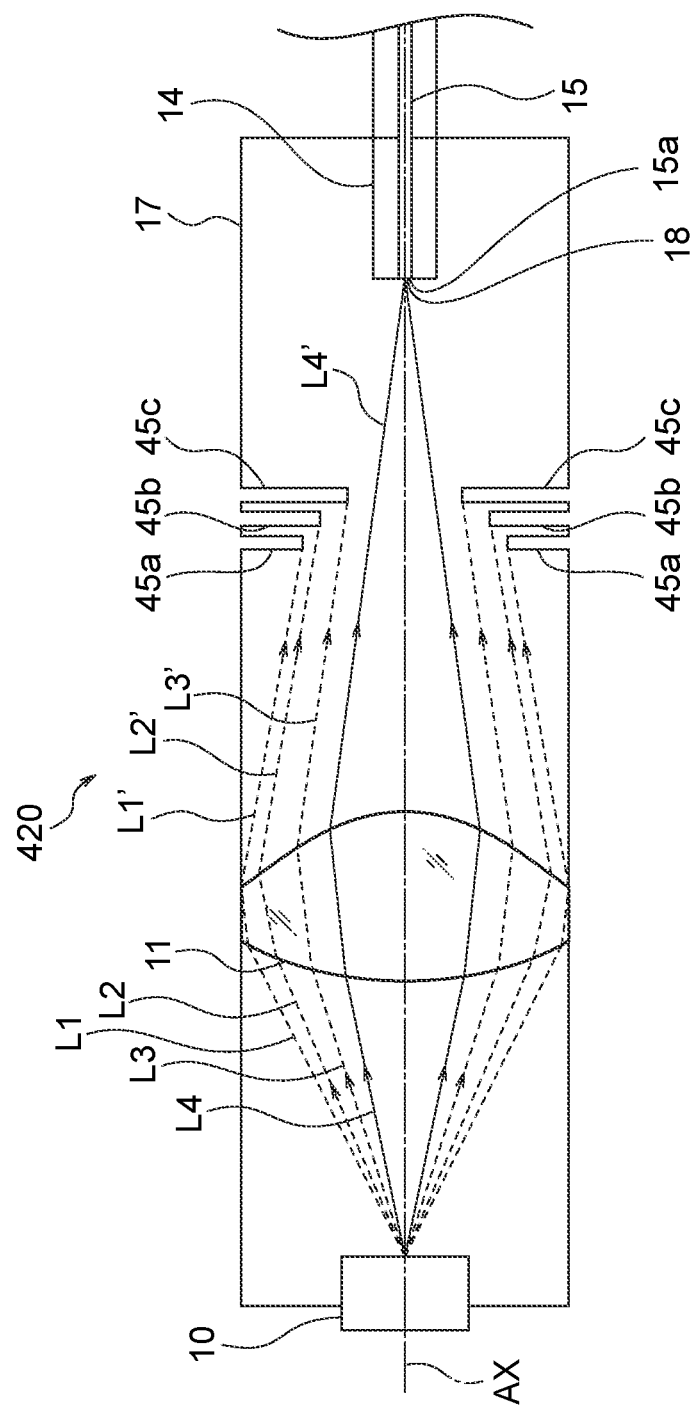
FIG. 8 is a cross-sectional view of a light source apparatus for endoscope of another modified embodiment of the fourth embodiment.

FIG. 8 is a cross-sectional view of an arrangement of a light source apparatus for endoscope 420 of a modified embodiment 2 of the fourth embodiment. In the present modified embodiment, the heat exhausting member also serves a function of plates 45a, 45b, and 45c. The plates 45a, 45b, and 45c are formed such that a diameter of an aperture of an opening of each plate becomes gradually smaller toward the optical fiber 15.

In the present embodiment, divergent lights L1, L2, L3, and L4 from the semiconductor laser 10 are converted to convergent lights L1', L2', L3', and L4' by the collective lens 11, and are incident on the plates 45a, 45b, and 45c.

The light L1' on the outermost side is shielded by the plate 45a. The light L2' is shielded by the plate 45b. The light L3' is shielded by the plate 45c. Transmitted light L4' which is not shielded by any of the plates 45a, 45b, and 45c is incident on the optical fiber 15. Accordingly, since an amount of light shielded can be shared by each of the plates 45a, 45b, and 45c, it is possible to distribute the heat generation to each plate. Therefore, it is possible to dissipate efficiently the heat to the outside of the pigtail 17.

Fifth Embodiment

It is preferable that in a light source apparatus for endoscope according to the present embodiment, the heat exchanging member and the heat diverging member are integrated with the light source. The light shielding member has a heat diverging member which is connected to at least one of the heat exchanging member and the heat diverging member, and which transfers heat to heat dispersion member upon uniformalizing a temperature by dispersing heat received from the heat exchanging member.

Figure 9:
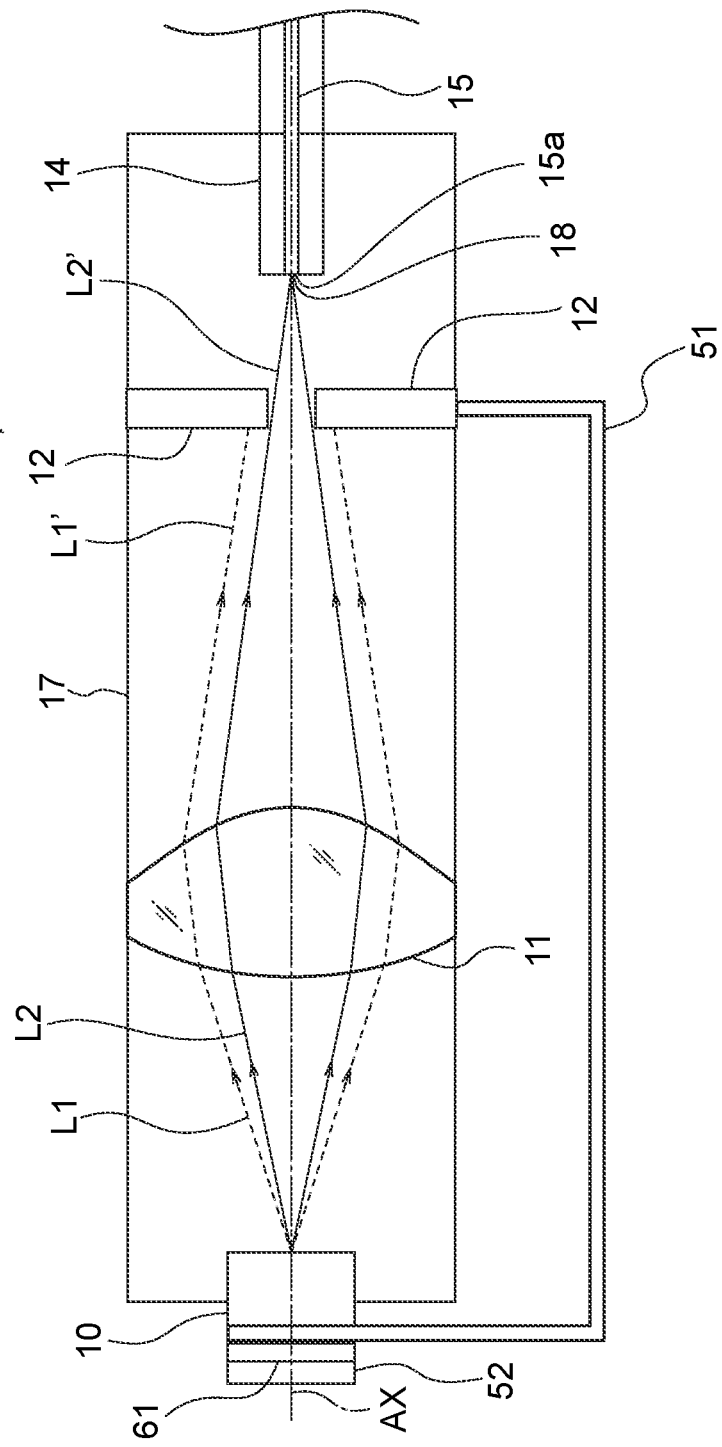
FIG. 9 is a cross-sectional view of a light source apparatus for endoscope of a fifth embodiment.

FIG. 9 is a cross-sectional view of an arrangement of a light source apparatus for endoscope 500 of a fifth embodiment. The semiconductor laser 10, which is the light source, emits visible light for instance. In the present embodiment, the semiconductor laser 10 emits divergent lights L1 and L2. The collective lens 11 has a positive refractive power. The collective lens 11 converts the lights L1 and L2 from the semiconductor laser 10 to convergent lights L1' and L2', and focuses the convergent lights L1' and L2'. The plate 12, which is the light shielding member, shields at least a part L1' after conversion of the lights L1 and L2 emitted from the semiconductor laser 10. The light L2', which is not shielded by the plate 12, is transmitted as transmitted light. The light L2' transmitted through the plate 12 is incident on the optical fiber 15. The pigtail 17, which is the holding member, holds at least one of the semiconductor laser 10, the collective lens L11, and the plate 12 by fixing at a respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 12 by fixing at the position thereof.

A heat sink 52 which is the heat diverging member and a Peltier element 61 which is the heat exchanging member are integrated with the semiconductor laser 10. A graphite sheet 51, which is the heat dispersion member, thermally connects the plate 12 and the Peltier element 61. Here, the term 'thermally connects' refers to a state in which the plate 12 and the Peltier element 61 are connected so that the heat is transferred by the graphite sheet 51.

The Peltier element 61 dissipates heat received from the graphite sheet 51 to a heat-dissipating side. Moreover, the heat sink 52 is connected to the heat-dissipating side of the Peltier element 61.

Accordingly, the Peltier element 61 and the heat sink 52 dissipate the heat generated by the semiconductor laser 10. Furthermore, the plate 12 is connected between the Peltier element 61 and the semiconductor laser 10 by the graphite sheet 51 which is the heat dispersion member. The Peltier element 61 is capable of transferring heat to the heat sink 52 upon uniformalizing the temperature by dispersing heat received from the graphite sheet 51. Therefore, it is possible to diverge the heat generated in the plate 12 to the surrounding atmosphere of the pigtail 17.

Sixth Embodiment

Figure 10:
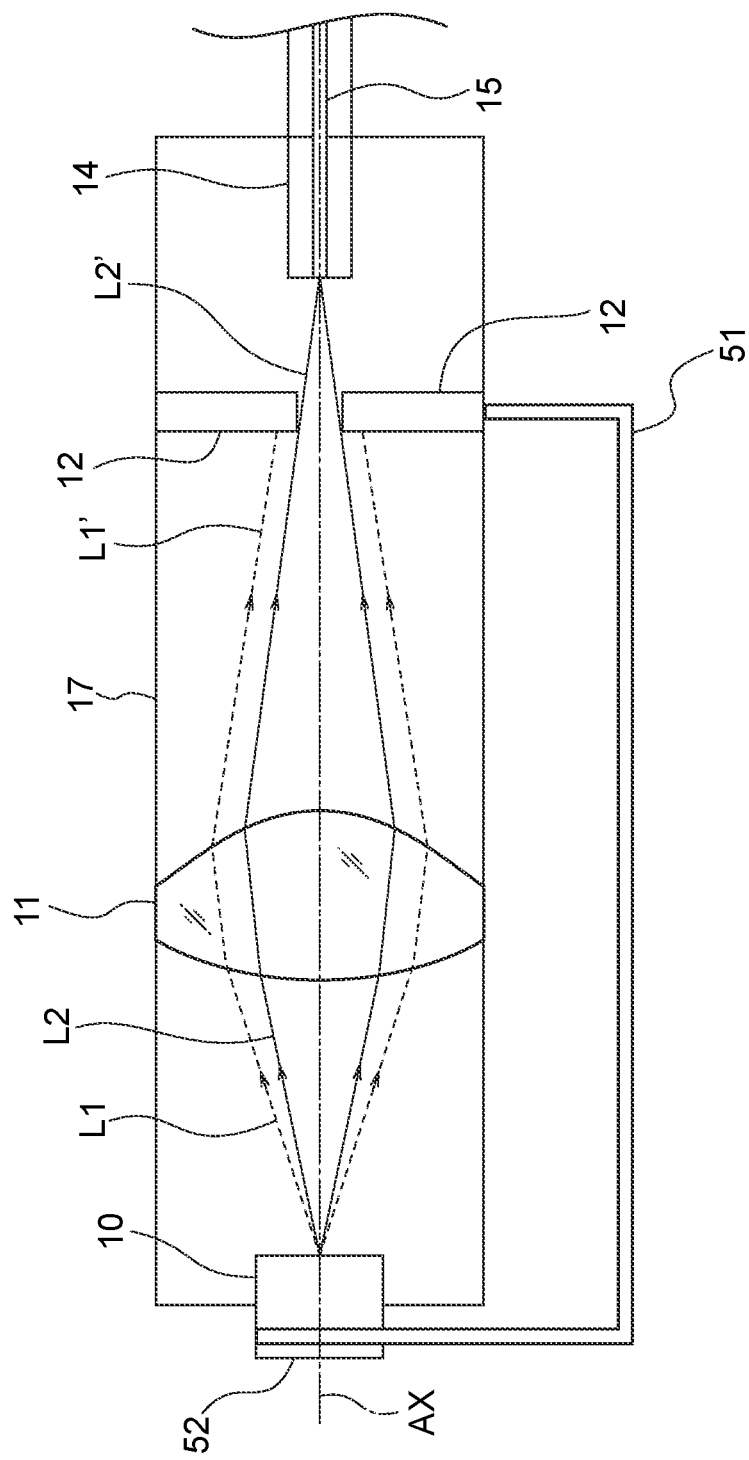
FIG. 10 is a cross-sectional view of a light source apparatus for endoscope of a sixth embodiment.

FIG. 10 is a cross-sectional view of an arrangement of a light source apparatus for endoscope 600 of a sixth embodiment. The semiconductor laser 10, which is the light source, emits visible light for instance. In the present embodiment, the semiconductor laser 10 emits divergent lights L1 and L2. The collective lens 11 has a positive refractive power. The collective lens 11 converts the divergent lights L1 and L2 from the semiconductor laser 10 to convergent lights L1' and L2', and focuses the convergent lights L1' and L2'. The plate 12, which is the light shielding member, shields at least a part L1' after conversion of the lights L1 and L2 emitted from the semiconductor laser 10. The light L2', which is not shielded by the plate 12, is transmitted as transmitted light. The light L2' transmitted through the plate L2' is incident on the optical fiber 15. The pigtail 17, which is the holding member, holds at least one of the semiconductor laser 10, the collective lens 11, and the plate 12 by fixing at a respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 12 by fixing at the position thereof.

The heat sink 52, which is the heat diverging member, is integrated with the semiconductor laser 10. The plate 12 is thermally connected between the semiconductor laser 10 and the heat sink 52 by the graphite sheet 51 which is the heat dispersion member. Here, the term 'thermally connected' refers to a state in which, the plate 12 and the heat sink 52 are connected so that the heat is transferred by the graphite sheet 51.

Accordingly, the heat sink 52 dissipates the heat generated by the semiconductor laser 10. Furthermore, the plate 12 is connected to the heat sink 52 by the graphite sheet 51, which is the heat dispersion member. The heat sink 52 dissipates the heat received from the graphite sheet 51. Consequently, it is possible to diverge the heat generated in the plate 12 to the surrounding atmosphere of the pigtail 17.

Seventh Embodiment

Figure 11:
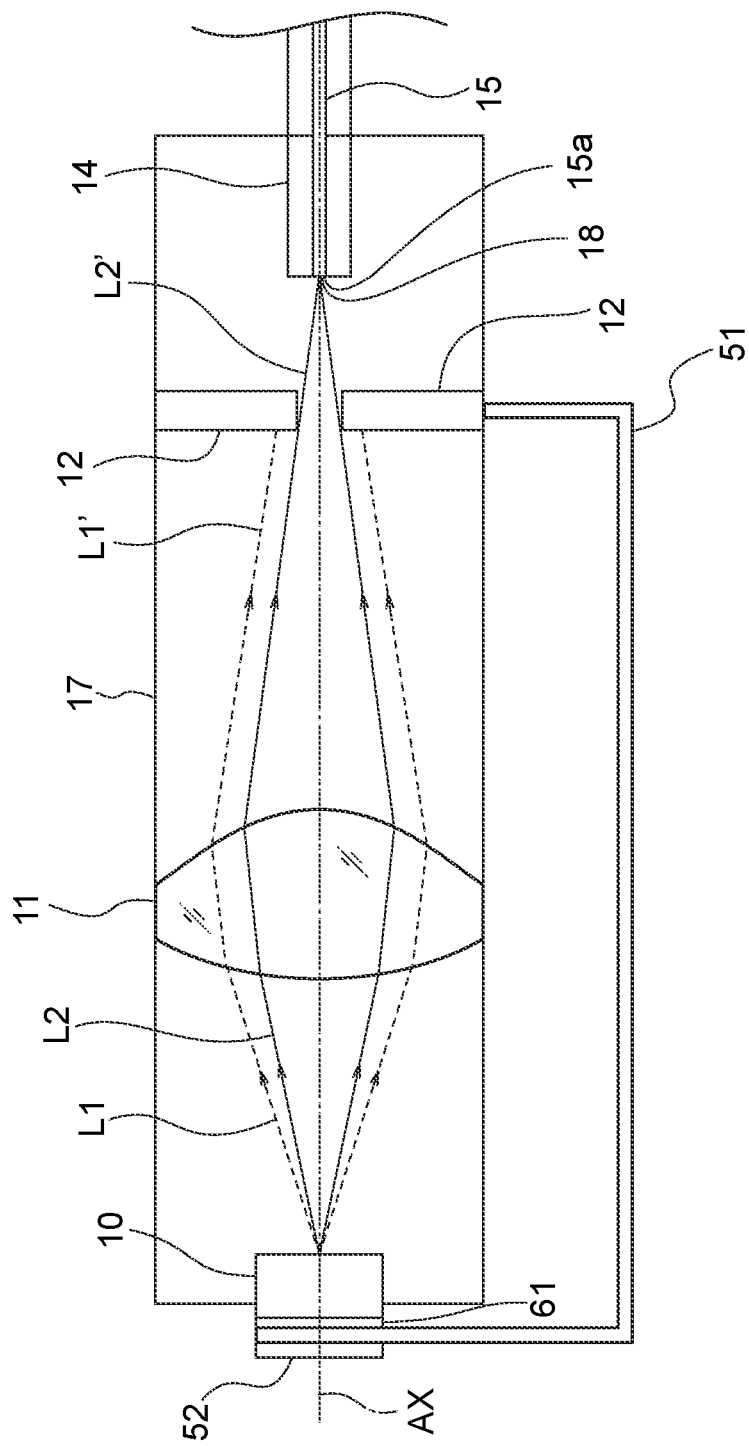
FIG. 11 is a cross-sectional view of a light source apparatus for endoscope of a seventh embodiment.

FIG. 11 is a cross-sectional view of an arrangement of a light source apparatus for endoscope 700 of a seventh embodiment. The semiconductor laser 10, which is the light source, emits visible light for instance. In the present embodiment, the semiconductor laser 10 emits divergent lights L1 and L2. The collective lens 11 has a positive refractive power. The collective lens 11 converts the lights L1 and L2 from the semiconductor laser 10 to convergent lights L1' and L2', and focuses the convergent lights L1 and L2. The plate 12, which is the light shielding member, shields at least apart L1' after conversion of the lights L1 and L2 emitted from the semiconductor laser 10. The light L2', which is not shielded by the plate 12, is transmitted as transmitted light. The light L2' transmitted through the plate 12 is incident on the optical fiber 15. The pigtail 17, which is the holding member, holds at least one of the semiconductor laser 10, the collective lens 11, and plate 12 by fixing at a respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 12 by fixing at the position thereof.

The Peltier element 61 which is the heat exchanging member and the heat sink 52 which is the heat diverging member are integrated with the semiconductor laser 10. The plate 12 is connected between the Peltier element 61 and the heat sink 52 by the graphite sheet 51 which is the heat dispersion member. The graphite sheet 51 is capable of transferring the heat to the heat sink 52 upon uniformalizing the temperature by dispersing heat received from the Peltier element 61.

Accordingly, it is possible to dissipate efficiently the heat generated in the plate 12 to the outside (surrounding atmosphere) of the pigtail 17.

Eighth Embodiment

Figure 12:
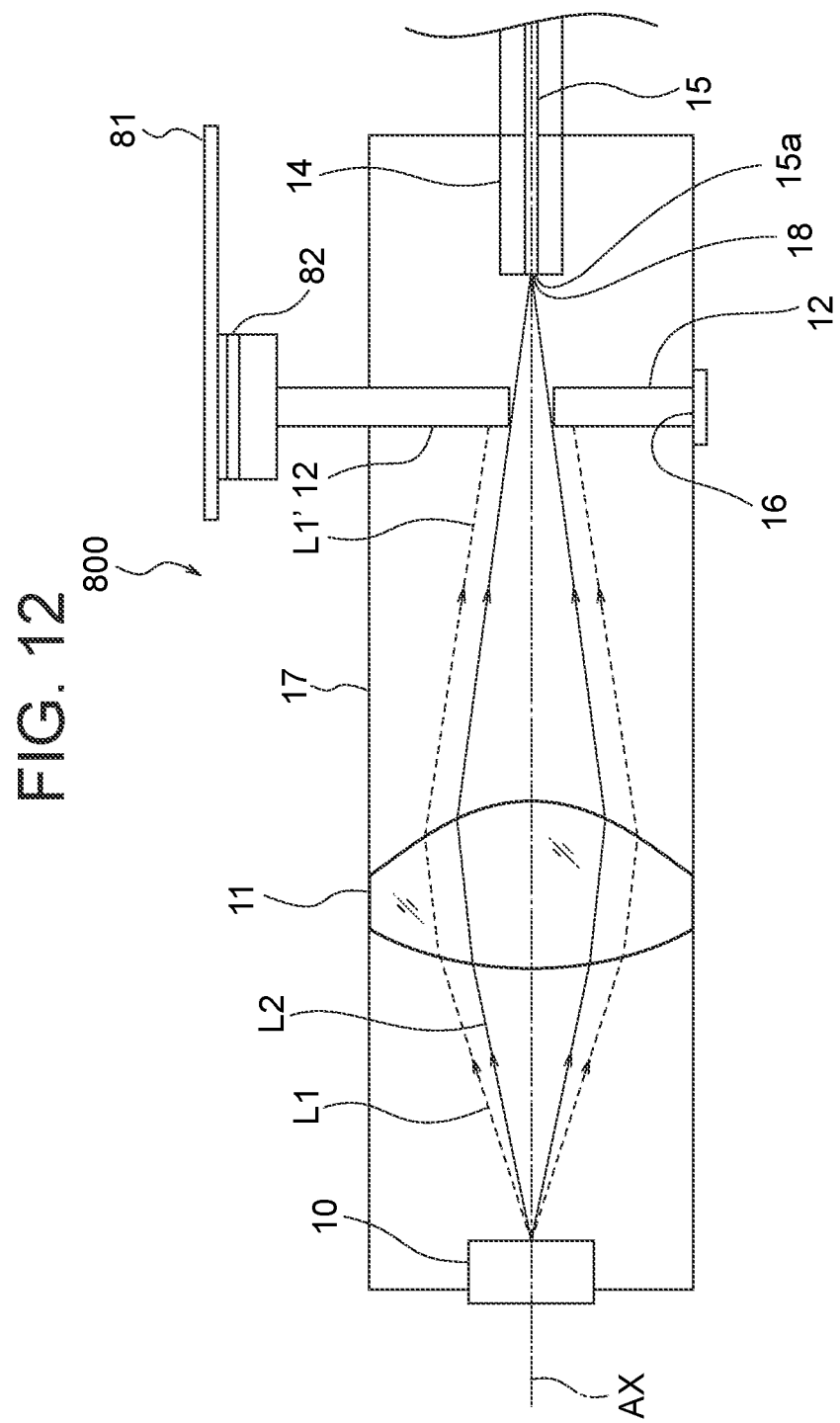
FIG. 12 is a cross-sectional view of a light source apparatus for endoscope of an eighth embodiment.

FIG. 12 is a cross-sectional view showing an arrangement of a light source apparatus for endoscope 800 of an eighth embodiment. The semiconductor laser 10, which is the light source, emits visible light for instance. In the present embodiment, the semiconductor laser 10 emits divergent lights L1 and L2. The collective lens 11 has a positive refractive power. The collective lens 11 converts the divergent lights L1 and L2 from the semiconductor laser 10 to convergent lights L1' and L2', and focuses the convergent lights L1' and L2'. The plate 12, which is the light shielding member, shields at least a part L1' after conversion of the lights L1 and L2 emitted from the semiconductor laser 10. The light L2' which is not shielded by the plate 12, is transmitted as transmitted light. The light L2' transmitted through the plate 12 is incident on the optical fiber 15. The pigtail 17, which is the holding member, holds at least one of the semiconductor laser 10, the collective lens 11, and the plate 12 by fixing at a respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 12 by fixing at the position thereof.

The plate 12 is thermally connected to a heat diffusion sheet 82. Moreover, the plate 12 is fixed to the pigtail 17 by the connecting portion 16. The heat diffusion sheet 82, for instance, is fixed to be in contact with an outer covering 81 of an operating section of an endoscope that will be described later. The outer covering 81 also serves a function of the heat diverging member.

Accordingly, it is possible to dissipate efficiently the heat generated in the plate 12 to the outside (surrounding atmosphere) of the pigtail 17.

Ninth Embodiment

Next, other problems to be solved will be described below. Relative positioning of members from the light source up to the end surface of the optical fiber is quite important. It is necessary to carry out this positioning easily and accurately. When the positioning is disrupted, it is not possible to focus effectively the light from the light source on the core of the optical fiber. Carrying out the relative positioning of the members from the light source up to the end surface of the optical fiber easily and accurately is also a problem which is to be solved.

An object of the present embodiment is to solve the abovementioned problem. It is preferable that the light source apparatus for endoscope of the present embodiment includes a light source which emits light, a collective lens which focuses the light emitted from the light source, a light shielding member which shields at least a part of the light emitted from the light source, and allows light which is not shielded, to be transmitted as transmitted light, an optical fiber on which the transmitted light transmitted through the light shielding member is incident, a holding member which holds at least one of the light source, the collective lens, and the light shielding member by fixing at a respective position thereof, and an optical fiber holding member which holds the optical fiber by fixing a position of an incident end of the optical fiber, on the basis of focusing position of the transmitted light.

Figure 13:
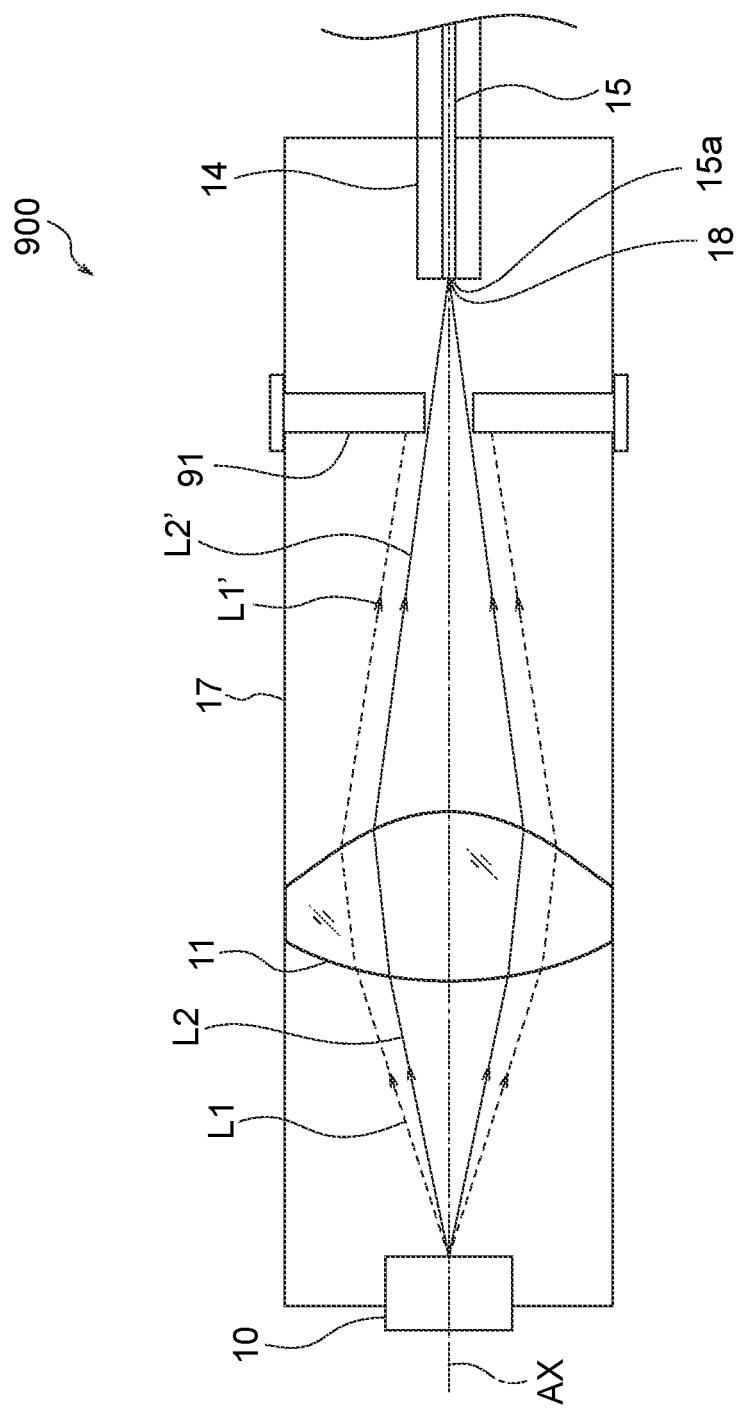
FIG. 13 is a cross-sectional view of a light source apparatus for endoscope of a ninth embodiment.

FIG. 13 is a cross-section view of an arrangement of a light source apparatus for endoscope 900 of a ninth embodiment. The semiconductor laser 10, which is the light source, emits visible light for instance. In the present embodiment, the semiconductor laser 10 emits convergent lights L1 and L2. The collective lens 11 has a positive refractive power. The collective lens 11 converts the divergent lights L1 and L2 from the semiconductor laser 10 to convergent lights L1' and L2', and focuses the convergent lights L1' and L2'. A plate 91, which is the light shielding member, shields at least a part L1' after conversion of the lights L1 and L2 emitted from the semiconductor laser 10. The light L2', which is not shielded by the plate 91, is transmitted as transmitted light. The light L2' transmitted through the plate 91 is incident on the optical fiber 15. The pigtail 17, which is the holding member, holds at least one of the semiconductor laser 10, the collective lens 11, and the plate 91 by fixing at respective position thereof. Specifically, the pigtail 17 holds the semiconductor laser 10 by fixing at the position thereof. Moreover, the pigtail 17 holds the collective lens 11 by fixing at the position thereof. Furthermore, the pigtail 17 holds the plate 91 by fixing at the position thereof.

Furthermore, the ferrule 14, which is the optical fiber holding member, holds the optical fiber 15 by fixing a position of the end surface 15d which an incident end of the optical fiber 15, on the basis of the focusing position 18 of the light L2' transmitted through the plate 91.

By inserting the ferrule 14 in to the pigtail 17, it is possible to make the focusing position 18 of the light L2' and the core 15a of the optical fiber 15 coincide.

Tenth Embodiment

It is preferable that an endoscope according to the present embodiment includes the abovementioned light source apparatus for endoscope, and an operating section, and the light source apparatus for endoscope is built-in in the operating section.

Figure 14:
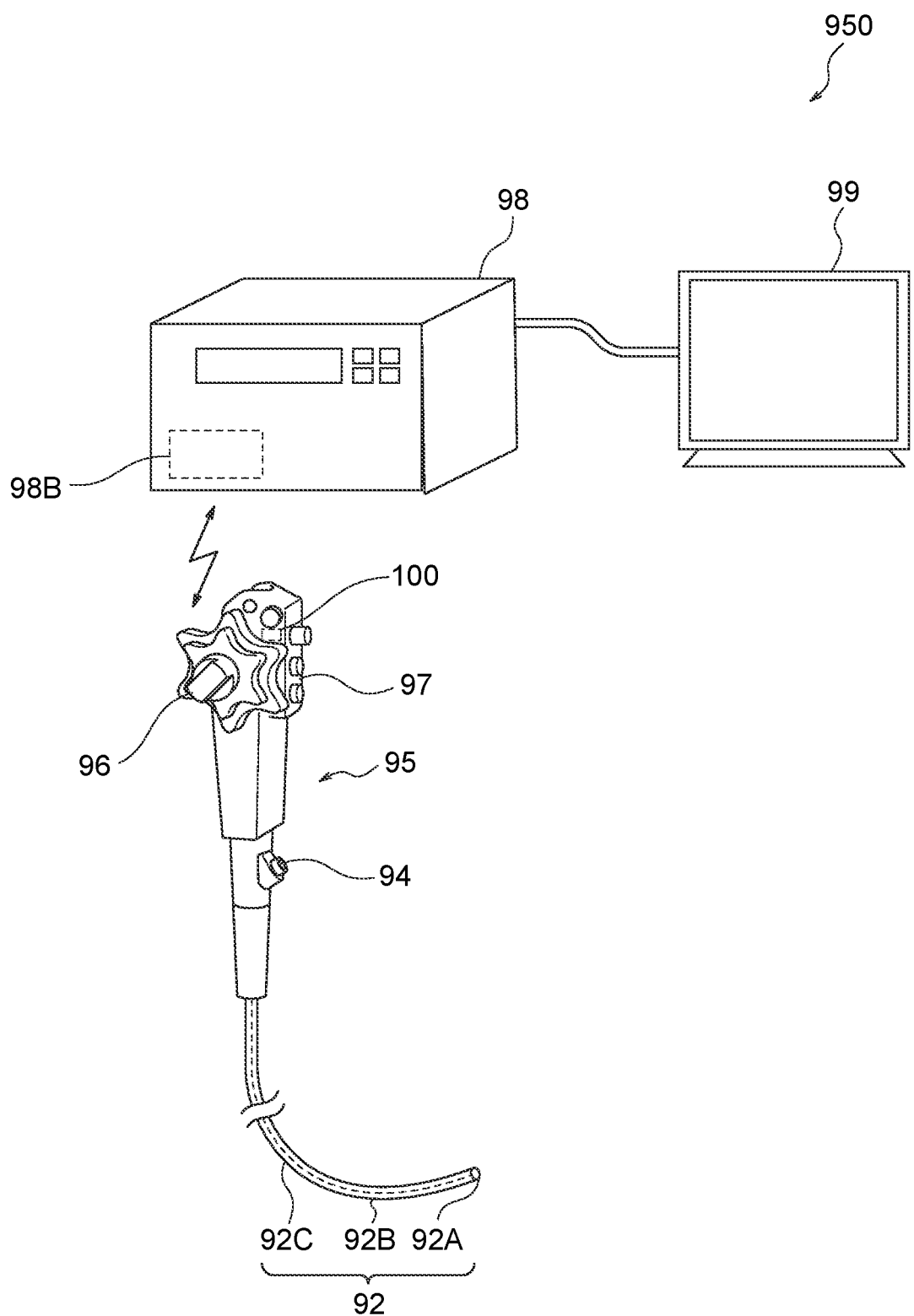
FIG. 14 is a schematic configuration diagram of a wireless endoscope of a tenth embodiment.

FIG. 14 is a schematic configuration diagram of an endoscope 950 according to the present embodiment. The endoscope 950 includes the abovementioned light source apparatus for endoscope 100 and an operating section 96. The light source apparatus for endoscope 100 is built-in in the operating section 96.

As shown in FIG. 14, the endoscope 950 includes the light source apparatus for endoscope 100 of the first embodiment, a video processor 98 as a signal processor which generates a standard video signal (image signal) upon a signal receiver 98B receiving a wireless-transmitted imaging signal from a wireless endoscope 95, and a monitor 99 as a display apparatus which displays an image corresponding to the standard video signal as an endoscope image, by the standard video signal generated by the video processor 98 being input thereto.

As shown in FIG. 14, the wireless endoscope 95 includes an insertion portion 92 which is long and slender, and has flexibility, and the operating section 96 which is provided at a rear end (base end) of the insertion portion 92. The insertion portion 92 includes a distal end portion 92A provided at a front end of the insertion portion 92, a curved portion 92B provided at a rear end of the distal end portion 92A, and a flexible tube portion 92C extended from a rear end of the curved portion 92B up to a front end of the operating section 96.

In the present embodiment, the light source apparatus for endoscope 100 is provided inside the operating section 96. Therefore, it is possible to allow the heat from the light source apparatus for endoscope 100 to be exhausted to an outer covering of the operating section 96. Consequently, it is possible to observe an object with highly efficient illumination light all the time.

In each of the abovementioned embodiments, the pigtail 17 may include a plurality of components.

The following invention is included in the present disclosure.

(Appended mode 1)

A light source apparatus for endoscope comprising:
a light source which emits light;
a collective lens which focuses the light emitted from the light source;
a light shielding member which shields at least a part of the light emitted from the light source, and allows a light which is not shielded, to be transmitted as transmitted light;
an optical fiber on which the transmitted light transmitted through the light shielding member is incident;
a holding member which holds at least one of the light source, the collective lens, and the light shielding member by fixing at a respective position thereof; and
an optical fiber holding member which holds the optical fiber by fixing a position of an incident end of the optical fiber, on the basis of a focusing position of the transmitted light.

The arrangement of each embodiment, even when used independently or used freely in a combination, shows the effects of the present disclosure. Moreover, the arrangement of each embodiment may be an arrangement that is modified independently, and similarly, will show the effects of the present disclosure.

As described heretofore, the present disclosure is useful for a light source apparatus for endoscope which is capable of shielding unnecessary light incident on the optical fiber, and to allow the heat generated by the shielded light to be exhausted to an outside of the apparatus, and an endoscope and a heat dissipation method using the light source apparatus for endoscope.

According to the present disclosure, it is possible to provide a light source apparatus for endoscope having a favorable efficiency of making light incident on the optical fiber, which enables efficient heat dissipation, and an endoscope and a heat dissipation method using the light source apparatus for endoscope.

What is claimed is:

1. A light source apparatus for endoscope comprising:
a light source configured to emit light;
a collective lens which focuses the light emitted from the light source;
a light shielding member which shields at least a part of the light emitted from the light source, and allows light, which is not shielded, to be transmitted as transmitted light;
an optical fiber on which, the transmitted light transmitted through the light shielding member is incident;
a holding member which includes a heat insulating member, and holds at least one of the light source, the collective lens, and the light shielding member, by fixing at a respective position thereof; and
a heat exhausting member which exhausts heat generated in the light shielding member to an outside of the holding member, wherein
a thermal resistance value in a thermal path of the light shielding member is smaller than a thermal resistance value of the heat insulating member,
a thermal resistance value in a thermal path of a connecting portion of the light shielding member and the heat exhausting member is smaller than the thermal resistance value of the heat insulating member, and
a thermal resistance value in a thermal path of the heat exhausting member is smaller than the thermal resistance value of the heat insulating member.

2. The light source apparatus for endoscope according to claim 1, further comprising:
an optical fiber holding member which holds the optical fiber by fixing a position of an incident end of the optical fiber, on the basis of a focusing position of the transmitted light.

3. The light source apparatus for endoscope according to claim 1, wherein
the heat exhausting member is thermally connected to the light shielding member, and
the light shielding member and the heat exhausting member are held by the holding member.

4. The light source apparatus for endoscope according to claim 1, wherein the light exhausting member is at least one of a heat exchanging member which actively transfers heat from the light shielding member, and a heat diverging member which diverges heat from the light shielding member to a surrounding atmosphere.

5. The light source apparatus for endoscope according to claim 4, wherein
the heat exchanging member and the heat diverging member are integrated with the light source, and
the light shielding member has a heat dispersion member which is connected to at least one of the heat exchanging member and the heat diverging member, and
the heat dispersion member transfers heat to the heat diverging member upon uniformalizing a temperature by dispersing heat received from the heat exchanging member.

6. The light source apparatus for endoscope according to one of claim 4, wherein at least one of the heat exchanging member and the heat diverging member diverges heat generated by the light source to the surrounding atmosphere of the holding member.

7. The light source apparatus for endoscope according to claim 1, wherein the light shielding member is a part of the holding member.

8. The light source apparatus for endoscope according to claim 1, wherein the heat exhausting member also serves a function of the light shielding member.

9. The light source apparatus for endoscope according to claim 1, further comprising:
an optical fiber holding member which holds the optical fiber by gluing at least apart of the clad of the optical fiber by an adhesive, the optical fiber having a core which guides light, and a clad disposed around an outer peripheral portion of the core and the clad has a refractive index lower than a refractive index of the core, wherein
the light shielding member, out of the light from the light source, allows light incident at a desired angle at a desired position on an incident end of the optical fiber to be transmitted as the transmitted light, and shields and absorbs light other than the transmitted light, and
the transmitted light is incident on the core and the clad.

10. The light source apparatus for endoscope according to claim 1, wherein
the light shielding member has an opening on a part thereof,
the light shielding member allows only light passed through the opening to be transmitted through the light shielding member, and makes incident on the optical fiber, and
the light shielding member is a light absorbing member which absorbs light from the light source irradiated to a portion other than the opening.

11. The light source apparatus for endoscope according to claim 10, wherein the opening has a shape which shields excess light that is not transmitted through the opening.

12. The light source apparatus according to claim 10, wherein the opening has a circular shape having a center which coincides with an optical axis of the light from the light source.

13. The light source apparatus according to claim 10, wherein
the light shielding member has an opening which is formed by not less than two light shielding plates that are movably disposed from an outer portion of the holding member, and
the opening allows to be transmitted more light in a short-axis direction than in a long-axis direction of a light-beam cross section, of the light from the light source.

14. The light source apparatus according to claim 10, wherein the light shielding member is disposed between the light source and the optical fiber.

15. The light source apparatus according to claim 14, wherein the light shielding member is disposed between the light source and the collective lens.

16. The light source apparatus according to claim 14, wherein the light shielding member is disposed between the collective lens and the optical fiber.

17. The light source apparatus for endoscope according to claim 10, wherein a surface of the light absorbing member which forms the light shielding member has an absorbing characteristic with respect to a wavelength of the light from the light source.

18. An endoscope comprising:
a light source apparatus for endoscope according to claim 1; and
an operating section, wherein
the light source apparatus for endoscope is built-in in the operating section.

19. A heat dissipation method which is a method of dissipating heat generated in a light shielding member which has shielded a part of light focused toward an incident end of an optical fiber by a collective lens, from the light emitted from alight source, the heat dissipation method comprising steps of:
transferring heat to a heat exhausting member by a light shielding member; and
exhausting heat to an outside of a holding member which holds at least one of the light source, the collective lens, and the light shielding member by fixing at a respective position thereof, by the heat exhausting member.

* * * * *